(12) United States Patent
Sonoda et al.

(10) Patent No.: US 9,671,133 B2
(45) Date of Patent: Jun. 6, 2017

(54) HEATING DEVICE (75) Inventors: Goro Sonoda, Osaka (JP); Hisamasa Kanki, Ibaraki (JP); Naoki Dobashi, Osaka (JP); Hiromichi Tanaka, Osaka (JP)

(73) Assignee: KOBAYASHI PHARMACEUTICAL CO., LTD., Osaka-shi (JP)

( * ) Notice: Subject to any disclaimer, the term of this patent is extended or adjusted under 35 U.S.C. 154(b) by 443 days.

(21) Appl. No.: 14/119,237

(22) PCT Filed: Jun. 8, 2012

(86) PCT No.: PCT/JP2012/064738
§ 371 (c)(1),
(2), (4) Date: Nov. 21, 2013

(87) PCT Pub. No.: WO2013/002006
PCT Pub. Date: Jan. 3, 2013

(65) Prior Publication Data
US 2014/0109891 A1    Apr. 24, 2014

(30) Foreign Application Priority Data

Jun. 28, 2011   (JP) ................. 2011-143334

(51) Int. Cl.
F24J 1/00    (2006.01)
A61F 7/03    (2006.01)
A61F 7/02    (2006.01)

(52) U.S. Cl.
CPC .............. *F24J 1/00* (2013.01); *A61F 7/034* (2013.01); *A61F 2007/0226* (2013.01); *A61F 2007/0258* (2013.01)

(58) Field of Classification Search
None
See application file for complete search history.

(56) References Cited

U.S. PATENT DOCUMENTS 4,066,078 A * 1/1978 Berg .................. A61B 5/04087
                                                      600/391
5,046,479 A * 9/1991 Usui .................... A61F 7/034
                                                      126/204

(Continued)

FOREIGN PATENT DOCUMENTS

JP    H5-208031    8/1993
JP    H7-80018     3/1995

(Continued)

OTHER PUBLICATIONS

International Search Report for International Application No. PCT/JP2012/064738 dated Aug. 14, 2012.

*Primary Examiner* — Gregory Huson
*Assistant Examiner* — Martha Becton
(74) *Attorney, Agent, or Firm* — Kratz Quintos & Hanson, LLP (57) ABSTRACT This invention provides a heating device ensuring sufficient adhesive force, even when it is removed from clothing and then reattached to different clothing. The heating device of the present invention comprises a bag unit 2 containing an exothermic composition A including an oxidizable metal that can generate heat by contact with air, one surface of the bag unit 2 being air-permeable; an adhesive layer 3 formed on the other surface of the bag unit 2; a first release sheet 4 provided on the adhesive layer 3 to cover the adhesive layer 3; and a second release sheet 5 provided on the first release sheet 4 to cover the first release sheet 4, wherein the first release sheet 4 has a release portion 41 and a residual portion 42; when the second release sheet 5 is removed from the first release sheet 4, the release portion 41 is removed together with the second release sheet 5 and the residual portion 42 remains on the adhesive layer 3.

6 Claims, 7 Drawing Sheets (56) References Cited

U.S. PATENT DOCUMENTS

| | | | | |
|---|---|---|---|---|
| 5,366,492 | A * | 11/1994 | Ueki | F24J 1/00 126/263.07 |
| 5,674,270 | A * | 10/1997 | Viltro | A61F 7/03 607/108 |
| 5,888,335 | A * | 3/1999 | Kobe | B32B 7/06 156/152 |
| 6,004,670 | A * | 12/1999 | Kobe | C09J 7/02 428/343 |
| 6,436,063 | B1 * | 8/2002 | Augustine | A61F 13/02 602/17 |
| 6,629,964 | B1 * | 10/2003 | Ono | A61F 7/03 602/48 |
| 6,886,553 | B2 * | 5/2005 | Yim | A61F 7/034 126/204 |
| 6,893,453 | B2 * | 5/2005 | Agarwal | A61F 7/034 607/108 |
| 8,790,384 | B2 * | 7/2014 | Uchiyama | A61F 7/02 607/112 |
| 2001/0010847 | A1 * | 8/2001 | Otsuka | A61F 7/034 428/36.1 |
| 2005/0196562 | A1 * | 9/2005 | Ota | A61F 7/034 428/34.1 |
| 2006/0173519 | A1 * | 8/2006 | Matsuo | A61F 7/034 607/108 |
| 2006/0282138 | A1 * | 12/2006 | Ota | A61F 7/03 607/96 |
| 2007/0108190 | A1 * | 5/2007 | Ferguson | A61F 7/007 219/545 |
| 2009/0188614 | A1 * | 7/2009 | Ota | A61F 7/034 156/256 |
| 2010/0023099 | A1 * | 1/2010 | Hidaka | A61F 7/034 607/108 |
| 2010/0087902 | A1 * | 4/2010 | Ota | A61F 7/034 607/112 |
| 2010/0161014 | A1 * | 6/2010 | Lynch | A61F 7/02 607/108 |
| 2010/0241199 | A1 * | 9/2010 | Hidaka | A61F 7/034 607/96 |
| 2010/0310854 | A1 * | 12/2010 | Nagami | A61F 7/02 428/316.6 |
| 2011/0076430 | A1 * | 3/2011 | Shigematsu | C09J 7/0207 428/35.2 |
| 2011/0126821 | A1 * | 6/2011 | Wilson | A47J 36/28 126/263.02 |
| 2014/0345595 | A1 * | 11/2014 | Nishioka | A61F 7/034 126/263.01 |
| 2015/0211766 | A1 * | 7/2015 | Yasuda | A61F 7/034 126/263.06 |
| 2015/0320589 | A1 * | 11/2015 | Nishioka | A61F 7/03 607/112 |

FOREIGN PATENT DOCUMENTS

| | | |
|---|---|---|
| JP | H7-284507 | 10/1995 |
| JP | 2001-145650 A1 | 5/2001 |
| JP | 3130652 U | 4/2007 |

* cited by examiner

HEATING DEVICE

TECHNICAL FIELD

The present invention relates to a heating device. More specifically, the present invention relates to a heating device that can be removed from and reattached to clothing.

BACKGROUND ART

Heretofore, so-called stick-on-type disposable chemical warmers to be attached to a user's clothing or the like have been widely used. Such chemical warmers have a flat bag unit having an air-permeable surface and, inside the bag unit, an exothermic composition containing an oxidizable metal that generates heat upon contact with air (for example, see Patent Document 1). Stick-on-type disposable chemical warmers have an adhesive layer opposite the air-permeable surface of the bag unit. The adhesive layer enables the chemical warmer to be adhered onto the user's clothing or the like.

CITATION LIST

Patent Document

PTL 1: JPH05-208031A

SUMMARY OF INVENTION

Technical Problem

Recent stick-on-type disposable chemical warmers can generate heat for a prolonged period of time. Therefore, for example, some warmers can also be used at home after being used at work or at school. When these stick-on-type disposable chemical warmers are continuously used after the user gets home, they are first removed from the work suit or school clothing, and then reattached to the home wear after the user has changed clothing. However, when these stick-on-type disposable chemical warmers are removed and reattached, the adhesive layer no longer has sufficient adhesive force because of dust or clothing fibers adhered thereto, and the warmers can easily come off from the clothing. In view of this problem, an object of the present invention is to provide a heating device that ensures sufficient adhesive force when the heating device is reattached to clothing after being removed from clothing.

Solution to Problem

The first heating device according to the present invention comprises a bag unit containing an exothermic composition including an oxidizable metal that can generate heat by contact with air, one surface of the bag unit being air-permeable; an adhesive layer formed on the other surface of the bag unit; a first release sheet provided on the adhesive layer to cover the adhesive layer; and a second release sheet provided on the first release sheet to cover the first release sheet, wherein the first release sheet has a release portion and a residual portion; and when the second release sheet is removed from the first release sheet, the release portion is removed together with the second release sheet, and the residual portion remains on the adhesive layer.

The heating device having such a structure is attached to the user as follows. By removing the second release sheet, the release portion of the first release sheet is removed together with the second release sheet. As a result, the portion covered with the release portion of the adhesive layer is exposed. The heating device is attached to the user using the exposed portion (first attachment). Then, when the heating device thus attached to the user is reattached to different clothing or a different part of the clothing, the heating device is first removed from the clothing, and the residual portion remaining on the adhesive layer is removed. As a result, a new portion of the adhesive layer, i.e., the portion that was not used for the first attachment, is exposed. The heating device is attached to different clothing or the like of the user using both the newly exposed portion and the previously used portion of the adhesive layer (second attachment). With such a structure, the heating device can be reattached to clothing two times with sufficient adhesive force.

The first release sheet is preferably divided into the release portion and the residual portion along an easy-cut line 43. By thus connecting the release portion and the residual portion while allowing them to be easily separated via the easy-cut line 43, the first release sheet and the second release sheet can be treated as a continuous sheet before they are adhered to the bag unit, thereby simplifying their handling. The easy-cut line 43 refers to a line that connects the release portion and the residual portion while allowing them to be easily separated. For example, the easy-cut line 43 may be provided by half-cutting, or by perforation. Further, the easy-cut line 43 enables, by simply removing the second release sheet, the release portion to be easily separated from the residual portion together with the second release sheet.

Further, the release portion is preferably provided on the entire circumference of the outer circumference of the adhesive layer. With this structure, at the first attachment, the removal of the release portion exposes the entire outer circumference of the adhesive layer 3. The heating device is attached to the user using the exposed portion (first attachment). As such, since the first attachment uses the outer circumference of the adhesive layer, the first attachment is stable.

Further, the residual portion may have a plurality of projections that extend toward the outer circumference of the adhesive layer. With this structure, since the residual portion has a plurality of projections extending toward the outer circumference of the adhesive layer, when the residual portion is removed from the adhesive layer at the second attachment, the portion of the outer circumference covered with the projections is exposed. Thus, the second attachment can also use the outer circumference of the adhesive layer.

Further, the second heating device according to the present invention comprises a bag unit containing an exothermic composition including an oxidizable metal that can generate heat by contact with air, one surface of the bag unit being air-permeable; an adhesive layer formed on the other surface of the bag unit; a first release sheet provided on the adhesive layer to cover a part of the adhesive layer; and a second release sheet provided on the adhesive layer via the first release sheet to cover the adhesive layer.

The second heating device having such a structure is attached to the user as follows. By removing the second release sheet, the portion not covered with the first release sheet of the adhesive layer is exposed. The second heating device is attached to the user using the exposed portion (first attachment). Then, when the heating device thus attached to the user is reattached to different clothing or a different part of the clothing, the heating device is first removed from the clothing, and the first release sheet 1 is removed to expose the adhesive layer thereunder. The heating device is attached to different clothing or the like of the user using both the newly exposed unused portion and the previously used portion of the adhesive layer (second attachment). With such a structure, the heating device can be reattached to clothing two times with sufficient adhesive force.

The second heating device may have variable structures. For example, the second heating device may have a structure in which the first release sheet is not provided in the outer circumference of the adhesive layer. With this structure, when the second release sheet is removed upon the first attachment, the outer circumference of the adhesive layer is exposed. As such, since the first attachment uses the outer circumference of the adhesive layer, the first attachment is stable.

Advantageous Effects of Invention

According to the present invention, the heating device ensures sufficient adhesive force, even when the heating device is removed from clothing and then reattached to different clothing.

DESCRIPTION OF EMBODIMENTS

An embodiment of the heating device of the present invention is described below with reference to the accompanying drawings.

Figure 1:
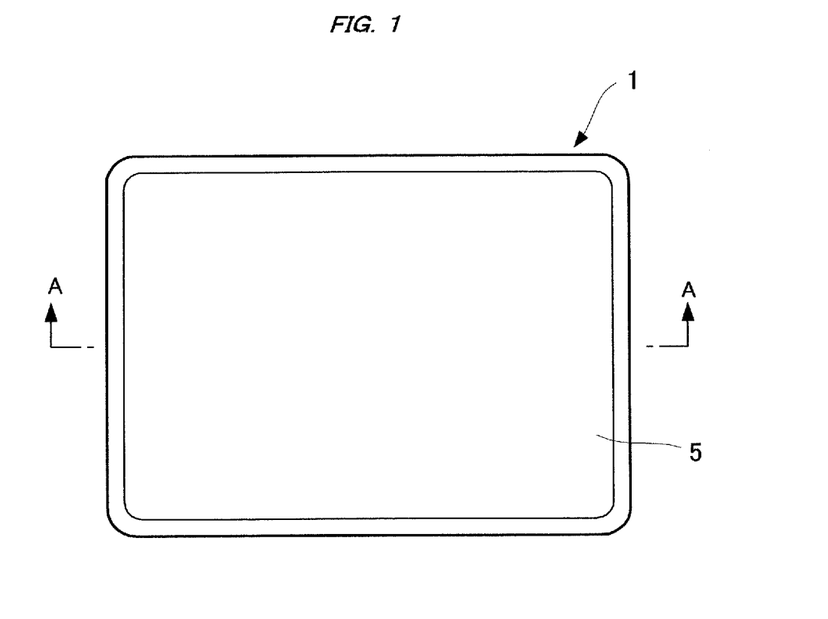
FIG. 1 is a plan view illustrating a heating device according to the present embodiment.
Figure 2:
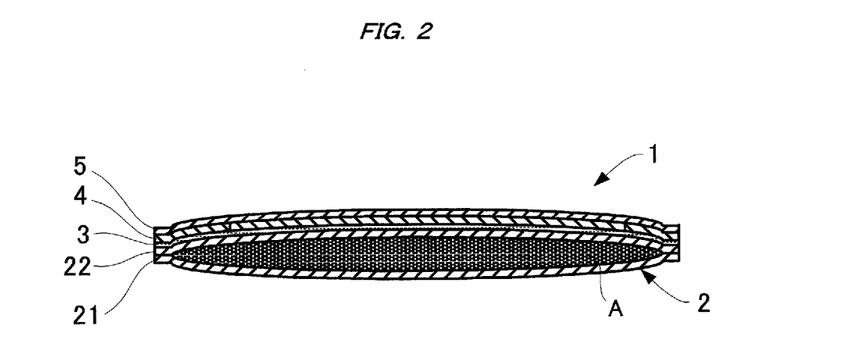
FIG. 2 is a cross-sectional view, taken along Line A-A in FIG. 1.

As shown in FIGS. 1 and 2, the heating device 1 includes a bag unit 2, an adhesive layer 3 formed on the upper surface of the bag unit 2, a first release sheet 4 covering the adhesive layer 3, and a second release sheet 5 covering the first release sheet 4.

Bag Unit

As shown in FIG. 2, the bag unit 2 is made as a flat bag by adhering the outer circumferences of the first sheet 21 and the second sheet 22 having a rectangular shape in a plan view by a heat-seal or the like. The bag unit 2 is filled with an exothermic composition A. The first sheet 21 is made of an air-permeable sheet. For example, preferably, a sheet has an air permeability of about 100 to 2000 $g/m^2/day$, more preferably about 200 to 1000 $g/m^2/day$, based on the water vapor transmission rate measured by JIS K7129100 Method A (humidity sensor method). The thus-defined first sheet 21 may have a single layer structure or a multilayer structure. As an example of multilayer structure, the first sheet 21 may be a lamination sheet in which a porous film and a non-woven fabric are overlaid. In this case, the porous film is disposed in contact with the exothermic composition. Examples of the materials of the porous film include urethane, polyethylene, and polypropylene. Further, examples of the materials of the non-woven fabric include polyester, polypropylene, nylon, rayon, and polyolefin. The second sheet 22 is made of a non-air-permeable sheet, and may have a single layer structure or a multilayer structure. As an example of a multilayer structure, the second sheet 22 may have a structure in which polyethylene copolymerized with a metallocene catalyst is placed on a sealant layer that is to be fixed to the first sheet 21. The sealant layer is processed to have a milky upper surface that serves as an intermediate layer so as to ensure the sealing of the exothermic composition. Further, a lamination polyethylene sheet having improved adhesion may be provided on the intermediate layer as a front layer.

Exothermic Composition

The exothermic composition A contained in the bag unit 2 is not limited insofar as it generates heat by contact with air. For example, a composition containing iron powder, a water-retaining agent, metal salts, and water may be used. The total mass of the iron powder, the water-retaining agent, the metal salts, and the water in the exothermic composition A is preferably about 80 to 100 mass %. The heating device of the present invention can exhibit the exothermic effect when the iron powder generates heat by reacting with oxygen in the air.

Examples of the iron powder include reduced iron and cast iron. These iron powders can be used alone or in combination. The iron powder may be in the form of granules, fibers, or the like. These forms of iron powders may be used alone or in combination. The particle size of the granular iron powder is typically within the range of about 10 to 300 µm, and preferably about 10 to 100 µm. The particle size as referred to herein can be determined as follows: one hundred grams of the test specimen (the iron powder or the like) to be measured is placed in an electric vibrating screen including, sequentially from the top, screens of 700 µm, 650 µm, 500 µm, 400 µm, 300 µm, 250 µm, 100 µm, 50 µm, and 10 µm; and vibrated for 15 minutes. The particle size can be subsequently determined by measuring the amount of the test specimen remaining in each screen and the amount of the test specimen passed through each screen. For example, when an iron powder with a particle size of 10 to 300 µm is used, an iron powder that has completely passed through the 300 µm screen, and remains on any or all of the 10 to 250 µm screens is used. The amount of the iron powder in the exothermic composition is preferably about 30 to 80 mass %, and more preferably about 45 to 65 mass %.

The water-retaining agent in the exothermic composition refers to a material capable of holding water. Examples of water-retaining agents include porous materials and water-absorbing resins. Specific examples of porous materials include activated carbon, wood flour, perlite, and vermiculite. Activated carbon is capable of capturing air into the micropores on its surface, thereby promoting oxygen supply; or of retaining heat, thereby keeping a constant heat-release temperature. The inside structure of activated carbon is very porous, and therefore provides a particularly good water-retaining ability. Furthermore, activated carbon absorbs well not only water, but also water vapor that evaporates upon generation of heat from the exothermic composition, thereby capturing the water vapor. As such, activated carbon can also be very useful as a water-retaining material. Additionally, activated carbon can also absorb odor emitted from the iron powder upon oxidation. Activated carbon prepared from, for example, coconut husks, wood, charcoal, coal, and bone black can be preferably used. The activated carbon may be in the form of granules, fibers, or the like. These forms of activated carbon may be used alone or in combination. In particular, in the present invention, granular activated carbon is preferably used. The particle size of the granular activated carbon is preferably about 10 to 300 μm, and more preferably about 10 to 100 μm. The particle size of the activated carbon is measured in the same manner as the particle size of the iron powder. Wood flour, perlite, and vermiculite may also take any form as long as they can retain water, but are preferably in granular form to improve the feeling of use of the heating device. The particle size of wood flour, perlite, or vermiculite in granular form is typically about 300 μm or less, and preferably about 250 μm or less. The particle size of wood flour, perlite, or vermiculite is also measured in the same manner as the particle size of the iron powder. Among these porous materials, activated carbon, and vermiculite are preferable; activated carbon and vermiculite are more preferable; and activated carbon is particularly preferable. These porous materials may be used alone or in combination.

Specific examples of water-absorbing resins used as the water-retaining agent include isobutylene-maleic anhydride copolymer, polyvinyl alcohol-acrylic acid copolymer, starch-acrylate graft copolymer, a polyacrylate crosslinked product, acrylate-acrylic ester copolymer, acrylate-acrylamide copolymer, and a crosslinked polyacrylonitrile. Preferable among these water-absorbing resins is a polyacrylate crosslinked product. The particle size of the water-absorbing resin is typically about 100 to 500 μm, and preferably about 250 to 400 μm. The particle size of the water-absorbing resin is also measured in the same manner as the particle size of the iron powder. These water-absorbing resins can be used alone or in combination. The porous materials and water-absorbing resins may be used alone or in combination as the water-retaining agent. The water-retaining agent used in the exothermic composition is preferably a porous material, or a combination of a porous material and a water-absorbing resin; more preferably activated carbon, or a combination of activated carbon, a porous material (other than activated carbon), and a water-absorbing resin; and still more preferably a combination of activated carbon, vermiculite, and a polyacrylate crosslinked product.

The amount of the water-retaining agent in the exothermic composition is preferably about 2 to about 30 mass %, and more preferably about 5 to about 20 mass %. More specifically, when a porous material is used alone as the water-retaining agent, the amount of the porous material in the exothermic composition is preferably 10 to 30 mass %, and more preferably about 10 to 20 mass %. When a water-absorbing resin is used alone as the water-retaining agent, the amount of the water-absorbing resin in the exothermic composition is preferably 2 to 10 mass %, and more preferably about 2 to 7 mass %. When a combination of a porous material and a water-absorbing resin is used as the water-retaining agent, the amounts of the porous material and water-absorbing resin in the exothermic composition are preferably 5 to 20 mass % and 1 to 10 mass %, respectively, and more preferably 7 to 20 mass % and 1 to 5 mass %, respectively. In particular, when a combination of activated carbon, a porous material other than activated carbon, and a water-absorbing resin is used as the water-retaining agent, the amounts of the activated carbon, porous material, and water-absorbing resin are preferably 3 to 20 mass %, 1 to 10 mass %, and 1 to 10 mass %, respectively, and more preferably 5 to 15 mass %, 1 to 5 mass %, and 1 to 5 mass %, respectively.

A metal salt facilitates the oxidation reaction with air, and therefore activates the surface of the iron powder to promote the oxidation reaction of the iron. Such metal salts may be selected from known metal salts generally used for exothermic compositions. Examples of such metal salts include sulfates such as ferric sulfate, potassium sulfate, sodium sulfate, manganese sulfate, and magnesium sulfate; and chlorides such as cupric chloride, potassium chloride, sodium chloride, calcium chloride, manganese chloride, magnesium chloride, and cuprous chloride. Carbonates, acetates, nitrates, and other salts can also be used. These metal salts can be used alone or in combination. The particle size of the metal salt is typically about 100 to 700 μm, and preferably about 250 to 650 μm. The particle size of the metal salt is also measured in the same manner as the particle size of the iron powder. The amount of the metal salt in the exothermic composition A is preferably about 0.5 to 10 mass %, and more preferably about 1 to 3 mass %.

Usable types of water include distilled water and tap water. The amount of water in the exothermic composition is preferably about 1 to 40 mass %, and more preferably about 20 to 30 mass %.

In addition to the above-described components, the exothermic composition A may optionally contain other additives that can be used in exothermic compositions. The exothermic composition A can be prepared by mixing the above-described components. Mixing may be performed under vacuum or an inert gas atmosphere, as required. Mixing may be performed according to, for example, the method described in U.S. Pat. No. 4,649,895.

Adhesive Layer

The adhesive layer 3 is provided in the outer surface of the second sheet 22. The adhesive layer 3 may be formed by applying, for example, an acrylic adhesive, a urethane-based adhesive, a silicone-based adhesive, a rubber-based adhesive, pine resin, or the like on the second sheet 22. The application amount of the adhesive is preferably adjusted so that the thickness of the adhesive is about 40 to 70 μm. A non-adhesive portion may be provided from one end to the other of the adhesive layer 3 along the long side or the short side of the adhesive layer 3. The non-adhesive portion may be provided, for example, by excluding this portion beforehand when the adhesive layer 3 is formed, or applying a non-adhesive substance on the portion after the adhesive layer 3 is formed. The thus-provided non-adhesive portion enables a residual portion 42 of the first release sheet (described later) to be more easily removed; therefore, when the user removes the heating device 1 attached to their clothing so as to reattach the heating device (second attachment), the user can insert a finger into the non-adhesive portion, thereby more easily removing the heating device. Examples of rubber-based adhesives include natural rubbers and synthetic rubbers such as SIS (styrene-isoprene-styrene) or SBR (styrene-butadiene rubber).

First Release Sheet

Figure 3:
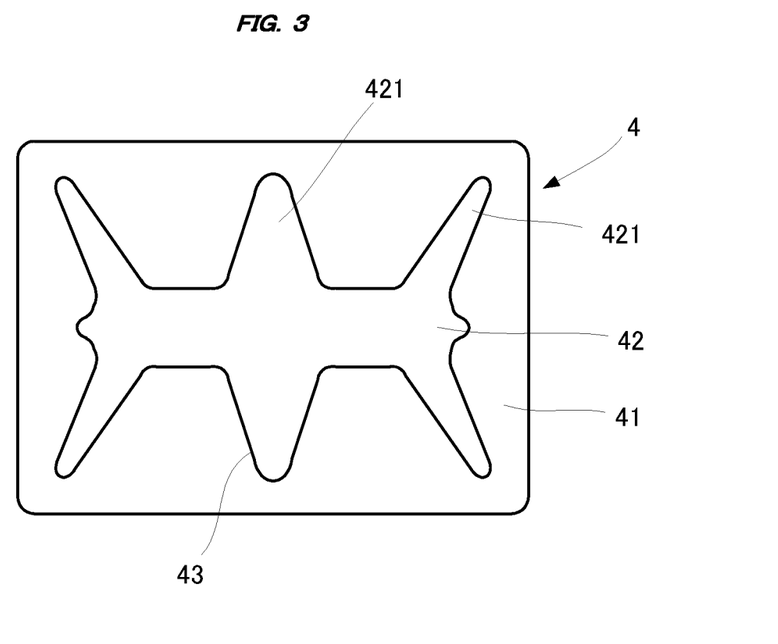
FIG. 3 is a plan view illustrating a heating device in which the second release sheet according to the present embodiment is omitted.

As shown in FIG. 3, the first release sheet 4 has the same rectangular shape as that of the adhesive layer 3, and covers the entire adhesive layer 3. The first release sheet 4 is divided into a release portion 41 and a residual portion 42 by an easy-cut line 43 provided by half cutting, and only the residual portion 42 is processed to hinder its adherence to the second release sheet 5 (described later) by, for example, applying a silicone resin on its upper surface (the surface facing the second release sheet 5). Accordingly, after the second release sheet 5 is removed, only the release portion 41 is removed together with the second release sheet 5, leaving the residual portion 42, which is not fully adhered to the second release sheet 5, on the adhesive layer 3. Examples of the materials of the first release sheet 4 include paper, polyethylene terephthalate, and polyethylene. They may be used solely or in combination.

The release portion 41 and the residual portion 42 may have various shapes; however, the release portion 41 preferably has a frame shape extending along the entire circumference of the outer circumference of the adhesive layer 3 so as to ensure adhesion of the outer circumference of the heating device 1 to the user's clothing without making gaps at the first attachment. Such a release portion 41 in the form of a continuous frame is also conducive to smooth removal of the release portion 41 together with the second release sheet 5 (described later) when the second release sheet 5 is removed.

The residual portion 42 preferably has a plurality of projections 421 that extend toward the outer circumference of the adhesive layer 3 so as to ensure newly exposed adhesive portions in the outer circumference upon the second attachment. Further, in the residual portion 42, all of the corners of the outer circumference are curved, thereby preventing partial removal of the residual portion 42 together with the second release sheet 5 upon removal of the later-described second release sheet 5. Further, the residual portion 42 may be provided with a slit extending across the two ends of the long side (horizontal direction in FIG. 3). This enables easy removal of the residual portion 42 from the slit. When the non-adhesive portion is formed on the adhesive layer 3, it is preferable to provide the slit of the residual portion 42 on the non-adhesive portion.

The proportion of the area of the release portion 41 to the entire area of the first release sheet 4; in other words, the proportion of the area of the adhesive layer 3 used for the first attachment to the entire area of the adhesive layer 3 is preferably about 62.5 to 87.5%, more preferably about 75.0 to 87.5%. With such an area proportion, as described later, the difference between the adhesive force of the first attachment and the adhesive force of the second attachment can be decreased. By thus adjusting the adhesive force of the adhesive layer 3, it is possible to fully attach the heating device 1 to the clothing both upon the first and second attachments, and prevent damage of the clothing when the heating device 1 is removed from the clothing. The adhesive force of the adhesive layer 3 in the portion covered with the release portion 41 and the portion covered with the residual portion 42 is preferably 10 to 30 N. By specifying the adhesive force to this range, the heating device 1 can be attached to the clothing with sufficient adhesive force, while preventing damage of the clothing upon removal of the heating device 1.

Second Release Sheet

The second release sheet 5 has the same rectangular shape as that of the first release sheet 4, and covers the entire first release sheet 4. The lower surface of the second release sheet 5, i.e., the surface facing the first release sheet 4 is an adhesive surface. The adhesive force of this adhesive surface of the second release sheet 5 with respect to the release portion 41 is greater than the adhesive force of the adhesive layer 3 with respect to the release portion 41; therefore, when the second release sheet 5 is removed, the release portion 41 of the first release sheet 4 is removed together with the second release sheet 5. As described above, since a silicone resin is applied on the upper surface of the residual portion 42, the adhesive force of the adhesive layer 3 with respect to the residual portion 42 is greater than the adhesive force of the adhesive surface of the second release sheet 5 with respect to the residual portion 42. Therefore, when the second release sheet 5 is removed, the residual portion 42 remains on the adhesive layer 3. Examples of the materials of the second release sheet 5 include paper, polyethylene terephthalate, and polyethylene. They may be used solely or in combination. Further, the adhesive surface may be formed from an acrylic adhesive, a urethane-based adhesive, a silicone-based adhesive, a rubber-based adhesive, pine resin, or the like. It is possible to also provide a slit on the second release sheet 5 to ease the removal. For example, the second release sheet 5 may have a slit extending across the two ends of the long side (horizontal direction in FIG. 1) in the center thereof.

Method for using Heating Device 1

The method for using the above-described heating device 1 is described below.

In the heating device 1, the exothermic composition A generates heat in the presence of air. Thus, the exothermic composition A must be prevented from contacting with air before the heating device 1 is used. Accordingly, the heating device 1 is usually contained in an airtight package. When the heating device 1 is used, the package is opened and the heating device 1 is taken out of the package.

Figure 4:
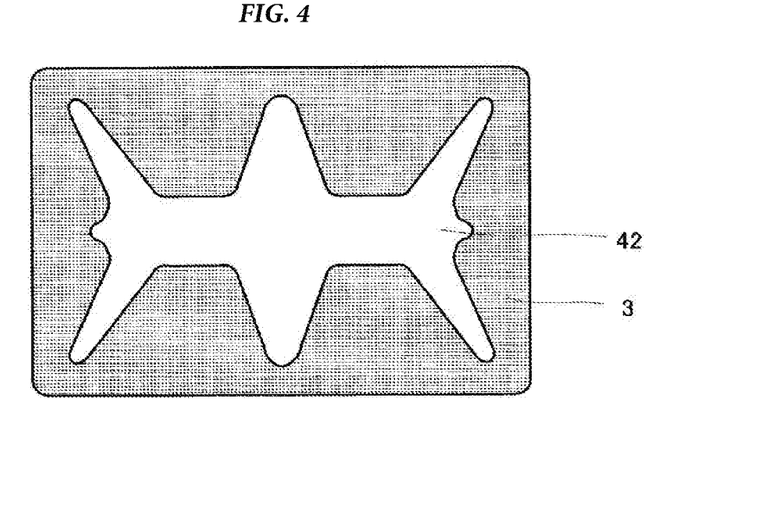
FIG. 4 is a plan view illustrating a heating device after the second release sheet according to the present embodiment is removed.

In order to attach the heating device 1 thus taken out from the bag, first, the second release sheet 5 is removed (first attachment). As a result, only the release portion 41 of the first release sheet 4 is removed together with the second release sheet 5, thereby exposing the adhesive layer 3 only in the portion that was covered with the release portion 41 (see FIG. 4). Using this exposed portion of the adhesive layer 3, the heating device 1 is attached to the clothing.

When the heating device 1 is reattached to clothing upon, for example, change of the clothing, first, the heating device 1 is removed from the clothing, and then the residual portion 42 of the first release sheet 4 is removed. As a result, the entire adhesive layer 3 is exposed. The heating device 1 is reattached to the clothing (second attachment) using the new adhesive portion of the adhesive layer 3 exposed by the removal of the residual portion 42, and also using the portion of the adhesive layer 3 used for the first attachment.

As such, according to the heating device 1 of the present embodiment, upon the first attachment, the heating device 1 is attached to clothing using a portion of the adhesive layer 3 covered with the release portion 41 of the first release sheet 4. Upon the second attachment, the heating device 1 is reattached to clothing by newly exposing the portion covered with the residual portion 42 of the first release sheet 4.

Thus, sufficient adhesive force can be ensured even in the second attachment of the heating device 1 to the clothing.

The present invention is not limited to the above-described embodiment, and can be modified in various ways within the spirit and scope of the invention.

Figure 5:
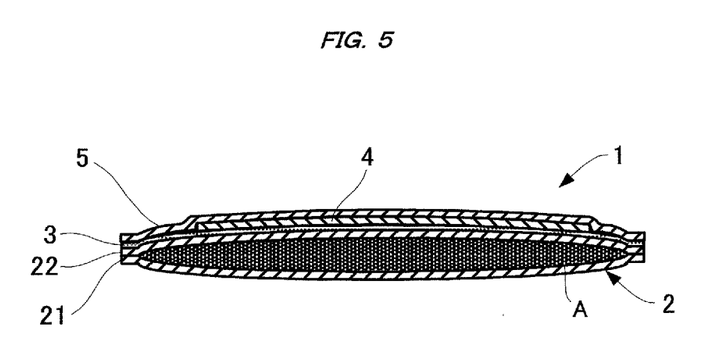
FIG. 5 is a front cross-sectional view showing a modification of the heating device according to the present embodiment.
Figure 6:
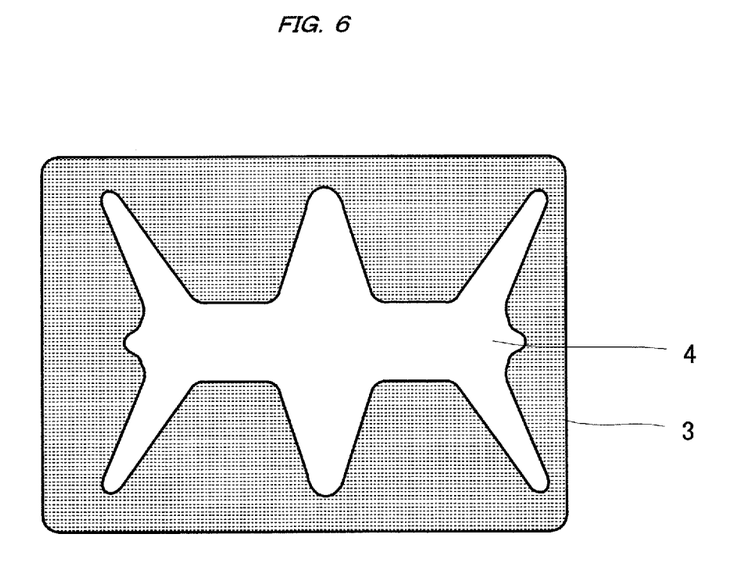
FIG. 6 is a plan view illustrating a modification of the heating device in which the second release sheet according to the present embodiment is omitted.

For example, although the first release sheet 4 covers the entire upper surface of the adhesive layer 3 in the above embodiment, it is also possible to, for example, provide the first release sheet 4 only in a part of the adhesive layer 3. For example, it is possible to adopt the structure shown FIG. 5 and FIG. 6 in which the first release sheet 4 is not provided in the outer circumference of the adhesive layer 3. Further, by using the second release sheet 5 and the adhesive layer 3 of equal size, the second release sheet 5 covers the first release sheet 4 and the outer circumference of the adhesive layer 3 that is not covered with the first release sheet 4. In the heating device 1 having such a structure, upon the first attachment, the outer circumference of the adhesive layer 3, which is not covered with the first release sheet 4, is exposed when the second release sheet 5 is removed. The heating device 1 is attached to the clothing using the exposed outer circumference of the adhesive layer 3. Thereafter, upon the second attachment, the first release sheet 4 is removed, and the heating device 1 is reattached to clothing using the newly exposed portion.

Further, although the first release sheet 4 in the above embodiment is structured such that the release portion 41 and the residual portion 42 are divided by half-cutting, and thus are partially connected, the present invention is not particularly limited to the structure. For example, the release portion 41 and the residual portion 42 may be completely separated. Optionally, the release portion 41 and the residual portion 42 may be divided in other ways, for example, by providing perforations.

Further, although the above embodiment provides adhesion between the second release sheet 5 and the release portion 41 by providing an adhesive layer on the lower surface of the second release sheet 5, the adhesion between the second release sheet 5 and the release portion 41 may be made by providing an adhesive surface on the upper surface of the release portion 41 instead of the lower surface of the second release sheet 5.

Figure 7:
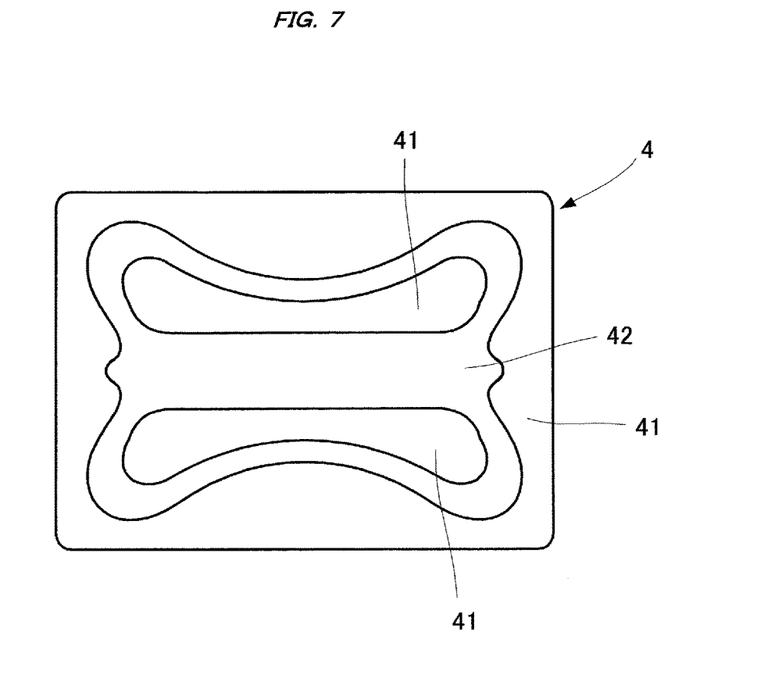
FIG. 7 is a plan view illustrating another modification of the heating device in which the second release sheet according to the present embodiment is omitted.
Figure 8:
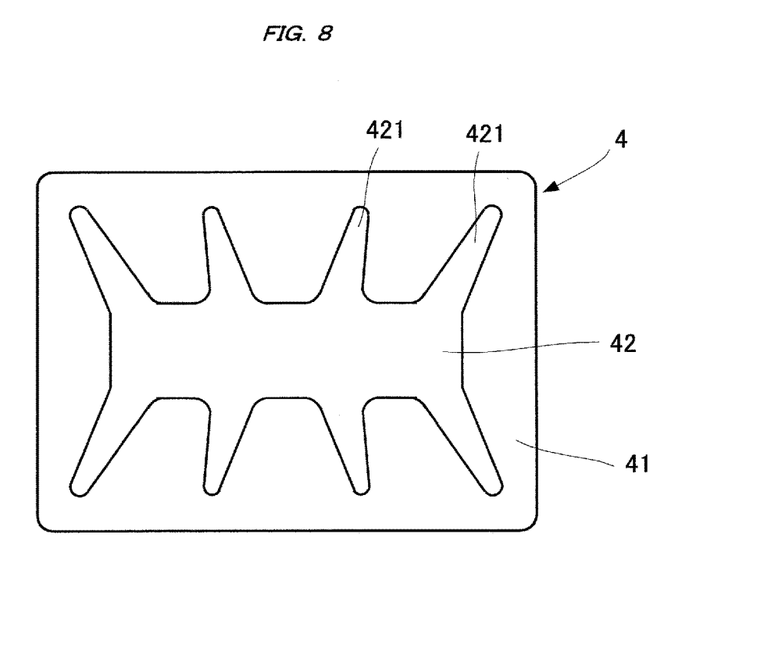
FIG. 8 is a plan view illustrating another modification of the heating device in which the second release sheet according to the present embodiment is omitted.
Figure 9:
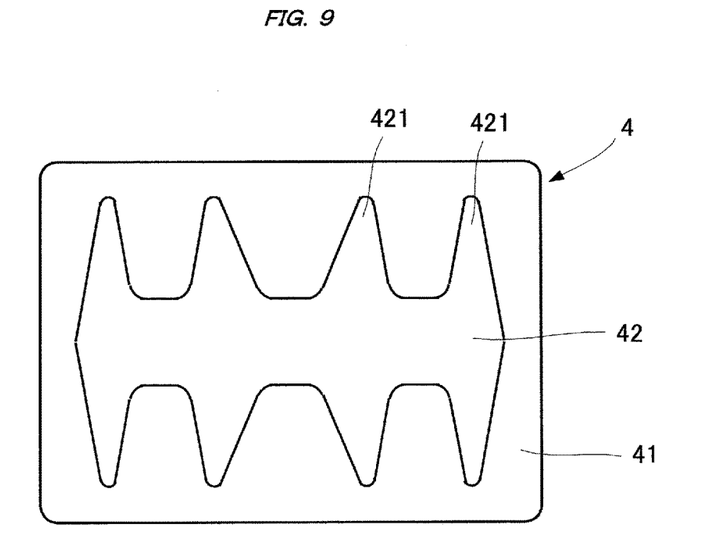
FIG. 9 is a plan view illustrating another modification of the heating device in which the second release sheet according to the present embodiment is omitted.
Figure 10:
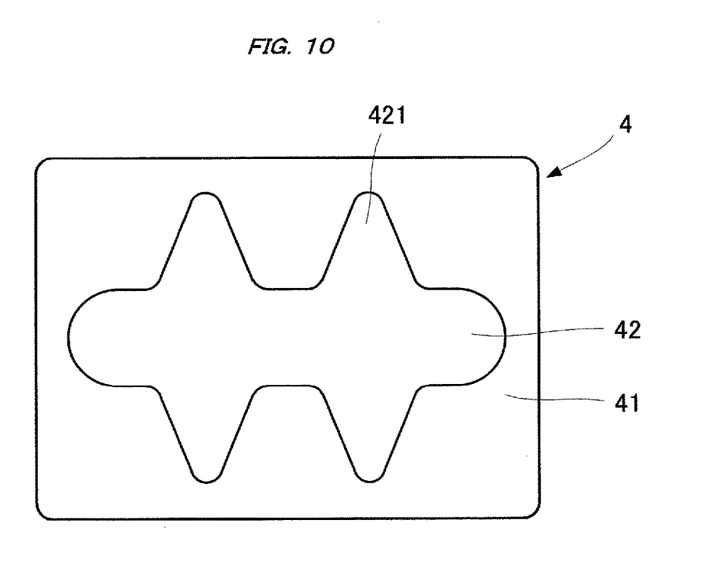
FIG. 10 is a plan view illustrating another modification of the heating device in which the second release sheet according to the present embodiment is omitted.
Figure 11:
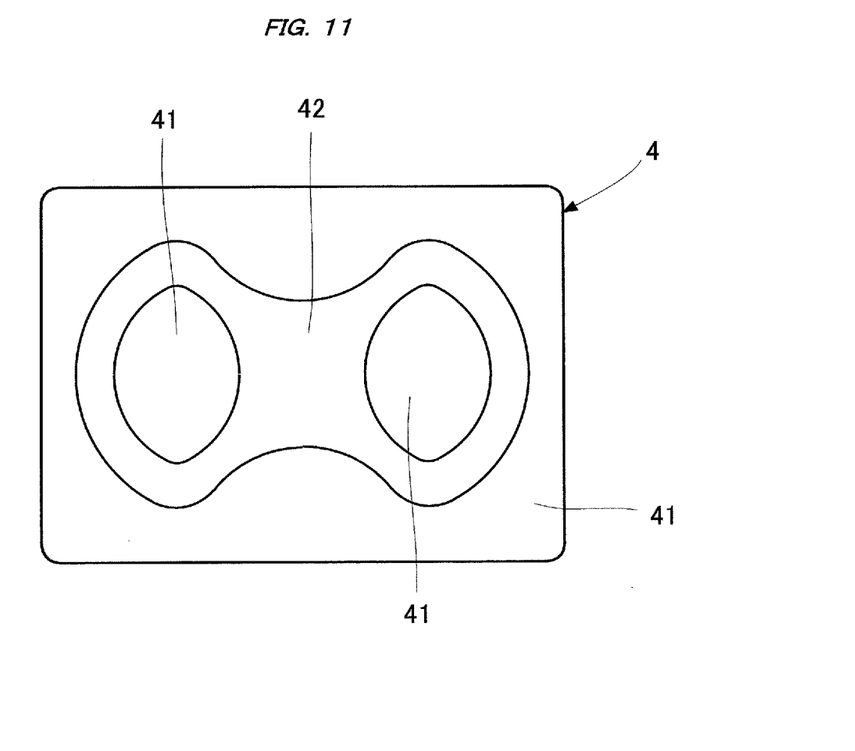
FIG. 11 is a plan view illustrating another modification of the heating device in which the second release sheet according to the present embodiment is omitted.
Figure 12:
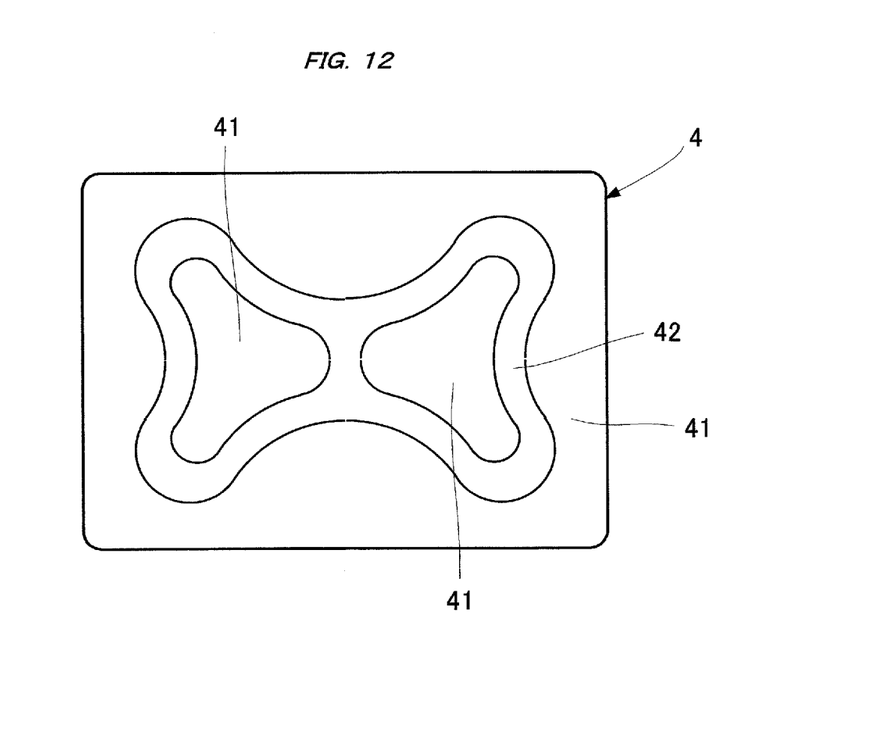
FIG. 12 is a plan view illustrating another modification of the heating device in which the second release sheet according to the present embodiment is omitted.
Figure 13:
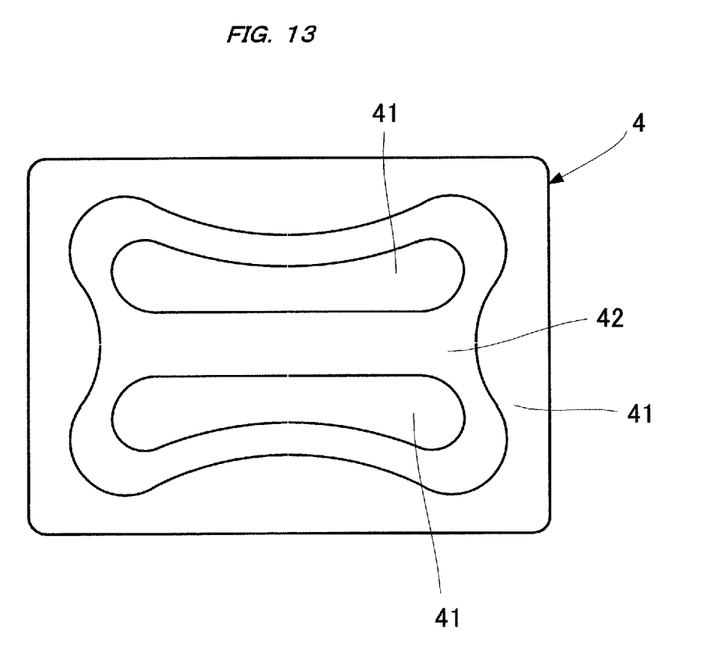
FIG. 13 is a plan view illustrating another modification of the heating device in which the second release sheet according to the present embodiment is omitted.

Further, the shapes of the first release sheet 4, the release portion 41, and the residual portion 42 are not limited to those in the above embodiment, and may be changed in various ways. For example, as shown in FIG. 7, it is possible to provide the release portion 41 not only in the outer circumference of the adhesive layer 3, but also inside the residual portion 42. In addition, the shapes shown in FIGS. 8 to 13 may also be used as the shapes of the release portion 41 and the residual portion 42 of the first release sheet 4.

REFERENCE NUMERALS 1 heating device
2 bag unit
3 adhesive layer
4 first release sheet
41 release portion
42 residual portion
421 projections
5 second release sheet

The invention claimed is:

1. A heating device comprising:
   a bag unit containing an exothermic composition including an oxidizable metal that can generate heat by contact with air, one surface of the bag unit being air-permeable;
   an adhesive layer formed on the other surface of the bag unit;
   a first release sheet provided on the adhesive layer to cover the adhesive layer; and
   a second release sheet provided on the first release sheet to cover the first release sheet,
   wherein the first release sheet has a release portion and a residual portion; when the second release sheet is removed from the first release sheet, the release portion is removed together with the second release sheet and the residual portion remains on the adhesive layer;
   the adhesive force of the residual portion with respect to the adhesive layer is greater than the adhesive force of the residual portion with respect to the second release sheet; and
   wherein the release portion is provided in the entire outer circumference of the adhesive layer.

2. The heating device according to claim 1, wherein the first release sheet is divided into the release portion and the residual portion along an easy-cut line.

3. The heating device according to claim 1, wherein the residual portion has a plurality of projections that extend toward the outer circumference of the adhesive layer.

4. The heating device according to claim 1, wherein the residual portion has a plurality of projections that extend toward the outer circumference of the adhesive layer.

5. A heating device comprising:
   a bag unit containing an exothermic composition including an oxidizable metal that can generate heat by contact with air, one surface of the bag unit being air-permeable;
   an adhesive layer formed on the other surface of the bag unit;
   a first release sheet provided on the adhesive layer to cover a part of the adhesive layer; and
   a second release sheet provided on the adhesive layer via the first release sheet to cover the first release sheet and the adhesive layer that is not covered with the first release sheet.

6. The heating device according to claim 5, wherein the first release sheet is not provided in the outer circumference of the adhesive layer.

* * * * *